United States Patent [19]

Beasley et al.

[11] 4,250,324

[45] Feb. 10, 1981

[54] WATER-DEGRADABLE ESTERS AND PROCESS FOR THE PREPARATION THEREOF

[76] Inventors: Marvin L. Beasley, P.O. Box 364, Alva, Okla. 73717; Norman G. Rhode, P.O. Box 626, Fayette, Iowa 52142

[21] Appl. No.: 852,722

[22] Filed: Nov. 18, 1977

Related U.S. Application Data

[63] Continuation of Ser. No. 607,578, Aug. 25, 1975, abandoned, which is a continuation-in-part of Ser. No. 342,058, Mar. 16, 1973, abandoned, which is a continuation-in-part of Ser. No. 197,309, Aug. 9, 1971, abandoned.

[51] Int. Cl.² ............................................. C07C 109/00
[52] U.S. Cl. ............................................. 560/62; 71/94; 71/115; 71/116; 71/117; 542/417; 542/418; 546/264; 560/47; 560/61; 560/65; 560/107; 560/110
[58] Field of Search ................... 560/110, 47, 61, 62, 560/65, 107

[56] References Cited

U.S. PATENT DOCUMENTS

| | | | |
|---|---|---|---|
| 2,469,358 | 5/1949 | Alderson et al. | 260/465.5 |
| 3,074,845 | 1/1963 | Geary | 424/23 |
| 3,343,941 | 9/1967 | Baltazzi | 71/71 |
| 3,481,972 | 12/1969 | Trepanier | 560/110 |
| 3,813,236 | 5/1974 | Allan | 71/94 |
| 3,916,010 | 10/1975 | Singer | 71/106 X |
| 3,962,329 | 6/1976 | Schoenaich et al. | 260/553 R |
| 3,984,451 | 5/1976 | Weiss et al. | 260/464 |
| 4,062,855 | 12/1977 | Allan et al. | 560/47 |

FOREIGN PATENT DOCUMENTS 2111804 10/1971 Fed. Rep. of Germany .

OTHER PUBLICATIONS

March, J., *Advanced Organic Chemistry*, McGraw Hill, New York, 1968, p. 674.
*Chemical Abstracts*, 52:14592h (1958) [Kost, A. et al., *Zhur. Obschei Khim.*, 28, 512–518 (1958)].
*Chemical Abstracts*, 57:11106h (1962) [Robinson, B. et al., VSP 3,031,291, 4/24/62].
*Chemical Abstracts*, 82:12137f (1975) [Mehltretter, C. et al., *Weed Sci.* 1974, 22(5), 415–418].

*Primary Examiner*—Henry R. Jiles
*Assistant Examiner*—Richard A. Schwartz
*Attorney, Agent, or Firm*—Browning, Bushman & Zamecki

[57] ABSTRACT

Water-degradable compounds formed from amine-type compounds, aldehydes and aromatic carboxylic acids, the respective components reacting to form a complex ester which upon contact with water slowly degrades to release, at least, the original carboxylic acid.

13 Claims, No Drawings

WATER-DEGRADABLE ESTERS AND PROCESS FOR THE PREPARATION THEREOF

RELATED APPLICATIONS

This is a continuation, of application Ser. No. 607,578, filed Aug. 25, 1975, now abandoned, which is a continuation-in-part application of our copending application, Ser. No. 342,058, filed Mar. 16, 1973 now abandoned, which in turn is a continuation-in-part of our prior application Ser. No. 197,309, filed Aug. 9, 1971, now abandoned.

BACKGROUND OF THE INVENTION

The present invention relates to novel, water degradable compounds and compositions and to a method of their preparation.

These exists numerous instances in which it is desirable to release an active ingredient at a controlled rate. For example, in the field of agriculture it would be extremely advantageous to have herbicides, fungicides, insecticides and other such agents released at a rate which would make maximum use of their properties.

Other than the aforementioned uses of the water degradable compositions of the present invention, there are several other areas, particularly concerned with agricultural usage, where the novel compositions herein have particular advantage. It is common practice, in applying insecticides, herbicides, fungicides, etc., to add the active ingredient in "spike" concentrations, i.e. concentrations above what is actually needed to achieve the desired effect. This is done in anticipation of runoff and migration of the chemical. Not only does such runoff and migration reduce the effectiveness of the active ingredients, but it can result in pollution of watersheds and underground water supplies. In a similar vein, the dissemination of agricultural chemicals by aircraft can result in serious problems due to the fact that in many cases the chemical in the form in which it is applied is subject to drift or misting. This drifting may result in the chemical being deposited on areas where it can cause damage to both plant life and wildlife. Accordingly, it would be most desirable to have a means of applying agricultural chemicals in such a fashion that such problems as runoff, migration, drifting or misting could be minimized.

SUMMARY OF THE INVENTION

It is therefore an object of the present invention to provide novel, water-degradable compounds.

It is a further object of the present invention to provide water-degradable compositions, in liquid or solid form, to enable such compositions to be adapted to a wide variety of end uses.

Still another object of the present invention is to provide water-degradable compounds in which are chemically incorporated certain biologically active ingredients which can be released at a controlled rate in the presence of water.

A further object of the present invention is to provide water-degradable compounds containing amine-type compounds, which compounds can have their water degradability controlled by the components from which they are made.

An important object of the present invention is to provide water-degradable compounds which incorporate certain biologically active ingredients which ingredients can be released in biologically active form upon degradation.

Another object of the present invention is to provide novel water-degradable compounds which can be used for encapsulating biologically or otherwise active ingredients which can be released at a controlled rate upon degradation of the encapsulating compounds.

A specific object of the present invention is to provide compounds used for controlled release of herbicidally active compounds.

It is another object of the present invention to provide a method of preparing water-degradable compounds so as to control their rate of water degradability.

Yet another object of the present invention is to provide a method for controllably releasing biologically active ingredients by including them into a water-degradable compound.

The above and other objects of the present invention will become apparent from the description given herein and the appended claims.

In one respect, the above objects are accomplished by providing a water-degradable compound made from an amine-type compound, an aldehyde and a carboxylic acid compound, the water-degradable compounds having the general formula:

$$\begin{array}{c} R_1-CH-NH-R_2 \\ | \\ O \\ | \\ O=C-R_3 \end{array} \qquad I$$

wherein $R_1$ is selected from the class consisting of $$\text{$\langle$phenyl$\rangle$}-CH=CH- \quad \text{and} \quad CH_3-CH=CH-$$

$R_2$ is selected from the class consisting of $$\begin{array}{cc} -NH-CH-R_1 & \overset{O}{\underset{\|}{-C}}-NH-CH-R_1 \\ | & | \\ O & O \\ | & | \\ O=C-R_3 & O=C-R_3 \end{array}$$

and $R_3$ is selected from the class consisting of phenyl$-O-C_aH_{2a}-$ where a is 1-3;

(Cl$_n$)phenyl$-O-C_bH_{2b}-$ where n is 2 or 3 and b is 1-3;

(Cl$_m$)phenyl$-$ where m is 1-3;

and a pyridine ring substituted with $NH_2$, Cl, Cl, Cl;

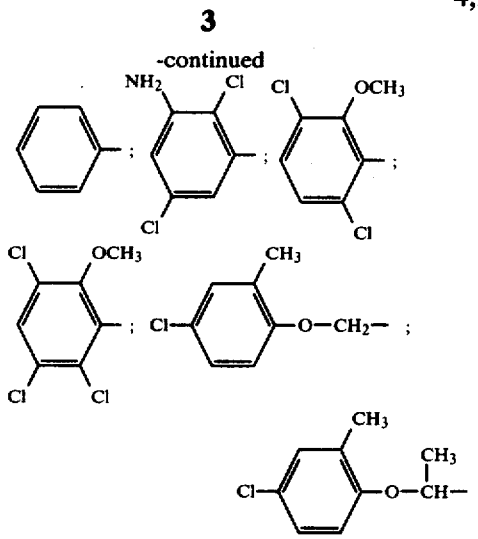
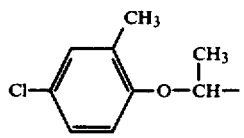

These water degradable compounds are prepared by reacting the respective compounds in either aqueous or organic media.

The water degradable compounds of the present invention degrade or "hydrolyze" in the presence of water to produce, at least, the carboxylic acid component of the compound. In a preferred embodiment, the compound can be tailored to accomplish controlled release, in the presence of water, of a biologically active compound such as a herbicide.

In employing the water degradable compounds of the present invention, a herbicide can be chemically incorporated into the compound itself or alternately an inert compound can be used to incorporate or encapsulate, in a physical mixture, an uncombined herbicide, the herbicide being controllably released as the encapsulating compound degrades.

DESCRIPTION OF THE PREFERRED EMBODIMENTS

The water-degradable compounds of the present invention, as can be seen above, contain as a basic part of their structure an amino grouping and an ester grouping. This complex ester formation results from reacting an amino type compound selected from the group consisting of hydrazine or urea, an aldehyde selected from the group consisting of cinnamic aldehyde or crotonaldehyde, and an aromatic carboxylic acid or its salt selected from the following group:

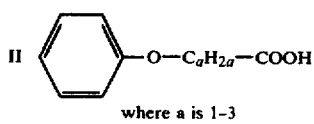

where a is 1–3

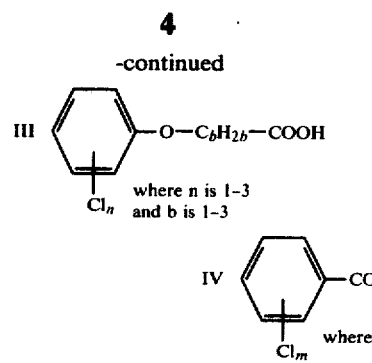

benzoic acid; 4-amino-3,5,6-trichloropicolinic acid; 3-amino-2,5-dichlorobenzoic acid; 2-methoxy-3,6-dichlorobenzoic acid; 2-methoxy-3,5,6-trichlorobenzoic acid; 2-methyl-4 chlorophenoxyacetic acid; 2-(2-methyl-4-chlorophenoxy) propionic acid;

Carboxylic acids useful in preparing the water-degradable compounds of the present invention and represented by Formula II include phenoxyacetic acid, 3-phenoxypropionic acid, 2-phenoxypropionic acid, 4-phenoxybutyric acid and the like. Carboxylic acids represented by Formula III which are useful in forming the water degradable compounds of the present invention include 2-4 dichlorophenoxyacetic acid (2,4-D), 2,4,5-trichlorophenoxyacetic acid (2,4,5-T), 2-(2,4,5-trichlorophenoxy) propionic acid, 2-(2,4-dichlorophenoxy) propionic acid, 4-(2,4-dichlorophenoxy) butyric acid and the like. The latter group of chlorinated phenoxy acids are particularly desirable for use in the present invention inasmuch as they exhibit herbicidal activity. A particularly useful carboxylic acid represented by Formula IV is 2,3,6-trichlorobenzoic acid which exhibits excellent herbicidal activity. Most of the carboxylic acids included in the above grouping exhibit herbicidal activity. While the unchlorinated phenoxy acids (Formula II) and benzoic acid do not exhibit herbicidal activity, they are quite useful insofar as the water degradable compounds of the present invention are concerned since they can be utilized to form "inert" water degradable compounds which, as will be seen hereafter, can be physically admixed with herbicidal materials to form a composition in which the herbicide is adsorbed or encapsulated in a water degradable matrix which, upon hydrolysis in the presence of water, will slowly release the uncombined herbicide. It is further to be observed that the moiety $R_3$ comprises one of the above carboxylic acids less the carboxyl group.

The reaction by which the water degradable compounds are formed, in the case where the amine type compound is hydrazine, is apparently as follows:

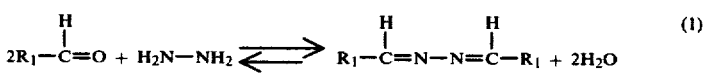

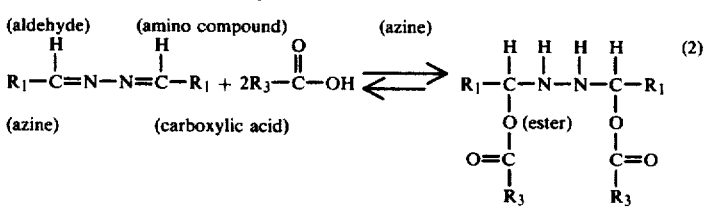

wherein $R_1$ and $R_3$ have the same scope as defined above.

In the case where the amine type compound is urea, the reaction is identical to that in equation (1) and (2) above and proceeds as follows:

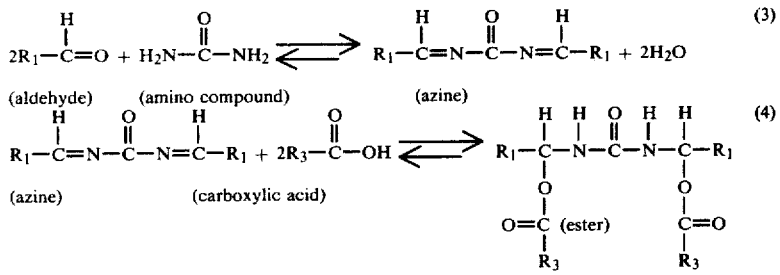

wherein $R_1$ and $R_3$ again have the scope as defined above. Thus, it is postulated that the reaction proceeds by way of the formation of an intermediate azine (equations 1 and 3) followed by the addition of the carboxylic acid to the C=N bond (Equations (2) and (4)).

That the water degradable compounds of the present invention have the above proposed general Formula I is substantiated by NMR and infrared spectra and by molecular weight determinations which have been conducted on compounds formed from many varied combinations of the amine type compounds, the aldehydes and the carboxylic acids.

As further substantiation for the proposed structure depicted in Formula I, cinnamic aldehyde and hydrazine were reacted to form cinnamalazine. The formation of the cinnamalazine was substantiated by a molecular weight determination on the product. The cinnamalazine was then reacted with 2-4 dichlorophenoxyacetic acid and the reaction product recovered. The latter reaction product was compared with the product obtained by reacting cinnamic aldehyde, hydrazine and 2-4 dichlorophenoxyacetic acid pursuant to the method of the present invention. Infrared spectra of both products were substantially identical providing further evidence that the structure of the water degradable compounds herein is as represented by Formula I.

In producing the compounds herein, the reaction may be carried out in either aqueous or non-aqueous, i.e. organic media. Turning first to the general method of preparation in aqueous media, the carboxylic acid compound, which preferably will be a herbicide, is dissolved in a solution of water and a miscible organic material such as acetone, methyl alcohol, ethyl alcohol, and the like. The amine-type compound, i.e. hydrazine or urea, is then dissolved in a solution of water and a miscible organic solvent such as acetone, methyl alcohol, ethyl alcohol or the like. Generally, acetone is the preferred organic solvent and it is generally preferred to dissolve the amine compound in a mixture of approximately 50-80% water and 50-20% acetone. The aldehydic compound, i.e. cinnamaldehyde or crotonaldehyde, is added to the aqueous solution of the amine-type compound at which point the carboxylic acid, dissolved in the aqueous media containing the water miscible organic solvent, is then added. To this mixture is added a small amount of a surfactant or emulsifier which, although not necessary, aids in stabilizing the reaction medium. The solution is then diluted with water and mixed thoroughly. At this point, the composition herein begins to form as evidenced by the fact that in most cases the solution changes generally to a reddish-brown color depending upon the particular components employed. Compounds produced in aqueous media in accordance with the above general procedure can have their rates of degradation controlled by varying the respective concentrations of the amine-type compound and/or the aldehydic material, or by varying the above two components and that of the carboxylic acid component.

In preparing the water-degradable compounds of the present invention in a non-aqueous or organic medium, the following general procedure is employed; the urea or hydrazine is dissolved in a suitable organic solvent such as methyl alcohol, acetone, methyl ethyl ketone, ethyl alcohol or the like. The carboxylic acid is dissolved in a suitable organic medium such as methyl alcohol, acetone, methyl ethyl ketone, ethyl alcohol, hydrocarbons such as distillation cuts from petroleum runs or the like. To the amine containing solution is added the aldehydic-type compound followed by addition of the carboxylic acid compound. A surfactant is then optionally added and the mixture is diluted with a suitable organic solvent and thoroughly mixed. As in the case of preparation in aqueous media, formation of the novel compounds herein is evidenced by color change in the solution. As in the case of the compounds produced in aqueous media, the rate of degradation of the compounds can be controlled by varying the same parameters as discussed above for the aqueous media preparation.

Theoretically, in preparing the compounds of the present invention, one molar equivalent of carboxyl group and one molar equivalent of aldehyde group is employed for each molar equivalent of amino hydrogen present in the amine-type compound. However, as a practical matter, it has been found in preparing the compounds herein, that all the available amino hydrogens do not react under the conditions employed. Thus, for example, when urea is employed as the amine-type compound, the molar ratios of urea to carboxylic acid to aldehyde will be in the ratio of 1:2:2 rather than 1:4:4. It is to be understood, however, that molar amounts of amino hydrogen present can be employed, the only requirement being that there be at least one equivalent of carboxyl group, one equivalent of aldehyde group and one equivelent of amino hydrogen be present to form the novel ester herein.

The process of the present invention, whether carried out in aqueous or non-aqueous media, can be conducted at room temperatures or at elevated temperatures depending on the particular components employed. It is preferable not to exceed the boiling point of the solvent medium at the pressure utilized. In the latter regard, the reaction can be carried out at atmospheric of superatmospheric pressures.

When the process of the present invention is carried out in an organic medium, virtually any inert, organic solvent or mixture thereof can be employed. It should be noted, however, that since materials such as carboxylic acids and aldehydes take part in the reaction, such materials should be avoided as solvents. In general, the solvent employed when the reaction is carried out in a non-aqueous media should be one which does not contain a reactive group which enters into the reaction with the amine-type compound. Thus, suitable solvents include alcohols (excluding glycols containing hydroxyl groups on adjacent carbon atoms) such as ethanol, methanol, propanol, isopropanol; ketones as for example acetone, methyl ethyl ketone, methyl isobutyl ketone and the like; ethers such as diethyl ether, dimethyl ether, diisopropyl ether, and the like; hydrocarbons such as benzene, toluene, diesel oil, mineral oil, kerosene, petroleum fractions such as for example Provalent 4-A, which is a mixed aliphatic-aromatic hydrocarbon petroleum cut; chlorinated materials such as carbon tetrachloride, chloroform, ethylene dichloride and the like; fluorinated materials such as the Freons, and other such compounds.

In like manner, when the reaction is carried out in a non-aqueous medium, the water miscible organic solvent employed therewith should be of a nature as described above for the solvents used in the purely organic media.

One group of solvents which can be employed when the reaction is carried out in an organic medium comprise the liquid surfactants or emulsifiers. In fact, it has been noted that when the compounds of the present invention are prepared in solution with a suitable surfactant, such solution may be dispersed in water without appreciable degradation of the compounds for some time, the surfactant apparently insulating the water-degradable compound from it aqueous surrounding for at least a reasonable period of time. Thus, a water-degradable compound can be prepared in an organic surfactant medium, then be dissolved in water and remain essentially undegraded for a short period of time. This, of course, is quite helpful since the water degradable compounds contain ingredients useful in agricultural application and thus it enables storing compositions containing the herbicidally active compounds and prevents them from degrading prior to spraying or other method of deposition. Once sprayed, however, the surfactant will evaporate leaving the water-degradable compounds which will subsequently release its active ingredients upon contact with moisture such as in a rainfall, irrigation, etc.

When a surfactant or emulsifying agent as described above is employed, it is preferred that it be one of the aryl modified polyglycol ethers such as a polyoxyethylene nonyl phenol or dodecyl phenol, or a polyoxyethylene sorbitan derivative such as polyoxyethylene sorbitan monolaurate, polyoxyethylene sorbitan monopalmitate, polyoxyethylene sorbitan monostearate and the like. In general, a large number of non-ionic surfactants can be employed based upon their relative inertness, their dissolving ability upon the components and the ultimate end use to which the water degradable materials are put.

The water degradable compounds of the present invention are particularly useful in formulating herbicidal compositions. As noted above, numerous herbicides contain carboxyl groups allowing them to be chemically combined in the compound. In a specific application of the use of one of the herbicidally active materials, the herbicide picloram (4-amino-3,5,6-trichloropicolinic acid) when reacted with urea and cinnamaldehyde makes a most effective compound for the control of ragweed. In this regard, the compound acts as a pre-emergent herbicide with corn. A composition of the picloram containing compound can also be effectively used as a defoliant. After being prepared, the composition is dissolved in an organic solvent or if desired prepared initially in such solvent. The solution is then sprayed on the foliage. The organic solvent evaporates leaving the defoliant (picloram), which is an integral part of the water-degradable compound on the foliage. At a time when sufficient moisture becomes available, such as after a rainfall, the picloram will be released from the compound and carry out the defoliating action. Likewise, other defoliants can be used in a similar fashion.

Because of the novel feature of the compounds of the present invention, i.e., their water degradability, they possess special advantages in use with herbicides in that they minimize pollution and maximize the efficiency of the herbicide. For example, since the compounds can be tailored to degrade at a preselected rate in the presence of water, they can retain the herbicide in such a fashion as to prevent excessive runoff under heavy rainfall conditions which can result in pollution of watersheds. Also, their retention of the herbicide prevents migration or percolation of the herbicide into underground supplies. Moreover, the compounds herein can be used to prepare herbicidally active materials for application by aircraft in such a fashion that the amount of drift or misting of the herbicide is controlled. It is known for example that certain herbicides while advantageously applied to certain plant growth in certain areas may adversely affect and even completely destroy other plant growth in adjacent areas. Thus in areas when adjoining acreages are producing different crops, control of drift of a given herbicide is extremely important.

The water-degradable compounds of this invention can also be employed as controlled release agents simultaneously for fertilizers and herbicides. For example, ammonium nitrate or phosphate fertilizers can be formulated or coated with a water-degradable compound made from a herbicide in a common solvent with subsequent removal of the solvent. The resulting solid product would include the fertilizer in a water-degradable, herbicide containing case, both of which could be released at a controlled rate. By coating a granular fertilizer, e.g., ammonium nitrate prills, with the water-degradable compounds herein formulated to have different degradation rates, a controlled release ammonium nitrate fertilizer can be achieved.

These compounds are singularly adaptable to agricultural uses since rainfall or irrigation will cause release of the active ingredient at the preselected rate determined by the level of degradability built into the compound during its production.

It is most convenient to spray herbicides or the like using an aqueous spray. Many of the compounds of this invention are insoluble, albeit degradable, in water. However, if the compounds are formed or dissolved in a non-ionic surfactant or emulsifying medium, such as a polyoxyethylene sorbitan monolaurate, the surfactant solution will permit the compounds to be dissolved in water. Furthermore, the surfactant appears to stabilize the compounds against degradation by the water in which it dissolved for a period of time of from about 24 to about 36 hours. Hence, the herbicidally active compounds can be formulated in water, and sprayed without any premature release of the herbicide.

When dealing with potentially toxic materials such as herbicides, and the like, the compounds of this invention offer the further advantage of reducing the effective human toxicity. Chemical incorporation of such toxic compounds reduces the toxic vapor which might be inhaled, and more importantly the absorption of toxic material through the skin is greatly reduced when the toxic compound is included in a water-degradable compound, and the skin could be cleansed with alcohol or the like. Even assuming that water contacts the water-degradable compound as a result of perspiration or washing, the release rate of the active ingredient e.g. the herbicide, is greatly reduced by inclusion in the compounds of this invention. If ingested, a water-degradable compound including a chemically bound herbicide would decompose slowly in a human's acid digestive tract and hence again produce a less toxic effect giving additional time for treatment.

Turning to non-agricultural uses, the novel compounds herein might incorporate acetylsalicylic acid and related analgesic compounds having carboxyl groups which may be incorporated in tablets in an otherwise benign water-degradable compound, and by incorporating these compositions in appropriate tablets, the medication can be made available at a controlled rate. Alternately, novel water-degradable compounds in accordance with this invention could be provided in a suitable liquid form, for example, in a suitable antiseptic pyrogen free, non-aqueous injectable fluid or the like, and injected into the body, rather than implanted as a solid capsule, and similarly effect the controlled release of an active agent.

It is known that organic acids can, at times, be painfully irritating to tissue and accordingly it may be desirable to incorporate a suitable buffer to minimize the tissue reaction to acid if such compositions are introduced within the body.

As previously noted, in applicants' prior application Ser. No. 170,309, the water-degradable compounds of the present invention were considered to be polymeric in nature. It was further thought that their rate of degradability could be controlled by heat treatment, the heat treatment affecting the polymeric structure. Since it is now believed that the compounds of the present invention have the structure as described above, i.e., a complex ester, the function of heating as regards degradability does not appear to be related to cross-linking or otherwise altering the molecular structure of a polymer but in fact appears to be related to driving the reaction to completion to obtain the ester formation. Thus, for example, if a given mixture of components having the functional groupings described above is heated for a prolonged period of time, a greater proportion of the water-degradable compound, i.e., the ester, is produced. As will be seen, these water-degradable compounds, i.e., the esters, slowly degrade in the presence of water.

Thus, for example, if heating is carried on for a sufficient time, and assuming stoichiometric amounts of the reactants are present, no unreacted components will remain. The resulting composition, i.e., the ester, will have a release rate which is determined by the nature of the components employed to form the compound. Thus, to the extent that heating of the solution drives the reaction to completion, i.e., to the ester formation, the length of time of releasability of the herbicide in the compound is heat dependent.

A particularly useful formulation involves the mixture of the water-degradable compounds herein containing a chemically bound herbicide agent in combination with the same but unreacted herbicide. In such a composition, the free or unbound herbicide is immediately available for usage upon application of the formulation while the chemically combined herbicide is released only through degradation upon contact with water and, accordingly, becomes available at a slow, controlled rate. Thus a residual activity is obtained.

In many cases it is desirable that the reaction be carried out until only a part of water-degradable compound is prepared. At this point there will remain unreacted ingredients, including the biologically active compound, and possibly other side reaction products. The temperature and time of heating which must be employed to achieve complete reaction of all the components to form the water-degradable composition will depend upon the precise components chosen. As a general rule, however, it has been found that reaction temperatures ranging from 30°–180° C. will suffice to form the compounds herein. Temperatures as high as 200° C. and higher may be employed; however, the temperature limitations will actually be determined by the thermal stability of reactants.

Since even trace amounts of the water-degradable compound, i.e., the ester, in the reaction mixture will serve to control releasability of the herbicide, it is not plausible to state a given range, in terms of amounts, of the ester which must be present since any amount will be effective.

In most of the examples which follow, the conditions of reaction were such that not all of the reactants combined to form the ester. Indeed, in those examples where very small amounts of aldehyde were employed relative to the amount of the amine-type compound and the carboxylic acid, only a small proportion of the ester was produced. Nonetheless, the presence of even small amounts of the water-degradable compounds herein serves the purpose of controlling the release rate of the unreacted herbicide. Thus, most of the examples demonstrate formulations comprised of the water-degradable compound containing chemically bound herbicide and unreacted and hence "encapsulated" herbicide.

The following non-limiting examples are illustrative of the invention. All amounts in the examples are by weight unless otherwise indicated.

EXAMPLE 1

A concentrate containing a water degradable composition of 2,4-D acid, urea and cinnamaldehyde was prepared. Urea (30 gm), 132 gm of cinnamic aldehyde and 221 gm of 2,4-D were dissolved in acetone with heat. During the course of the reaction a reddish-brown color began to form in the solution. The resultant product was sticky having a viscosity similar to heavy syrup at room temperature. Heating caused increased viscosity. The material was soluble in acetone. When water is added to an acetone solution of the product, an immediate precipitate occurs, one of the components being identifiable as 2,4D.

EXAMPLE 2

A material containing a water-degradable compound comprising dicamba (3,6-dichloro-O-anisic acid), urea and cinnamic aldehyde was prepared in a concentrate as follows: Urea (0.42 lb) was dissolved in a minimum amount of methanol. To this was added 0.04 lb of cinnamic aldehyde quickly followed by the addition of 6 lb of dicamba crystals. The volume was brought to one gallon with methanol and the concentrate heated to 70° C. to dissolve all the components. As the water degradable composition formed, a reddish-brown color was imparted to the solution. The material obtained by evaporation of the solvent was very sticky having a viscosity similar to that of heavy syrup. At lower temperatures, the material became more rigid having the consistency of paraffin or paste wax. To obtain a harder material it can be heated to a slightly elevated temperature. If the concentrate prepared above is to be stored for any length of time, it is desirable to add 3-5% of a surfactant such as Tween 20. The dicamba concentrate is extremely soluble in most organic solvents. Dilutions of 10:1 or greater can be accomplished without the active material, i.e. the dicamba acid, precipitating out of solution. If it is desired to form an aqueous spray from the above concentrate, the desired amount of concentrate and 1-2% of a surfactant are added to water. Such a solution is stable for approximately six weeks before degradation occurs and several months before precipitation of the dicamba acid occurs.

EXAMPLE 3

As previously noted, the novel compositions of the present invention are quite effective in reducing pollution hazards caused by leeching and/or lateral mobility of pesticides, herbicides and the like. For example, herbicidal compositions prepared in accordance with the above methods have been applied on the upper portion of a slope having a grade of 30°, the lower portion of which had stands of mustard, rye and tomato plants growing. To test the effectiveness in reducing lateral mobility of the herbicides, sprays of commercially available herbicides were compared with sprays of compositions of the present invention. The materials of the present invention and the commercial preparations contained equivalent amounts of the active ingredients. The tests were conducted under conditions wherein the rainfall amounted to ½ inch per day. The results of the tests are shown in the table below.

|  |  | % KILL | | | |
| --- | --- | --- | --- | --- | --- |
|  |  | 1st day | 2nd day | 4th day | 8th day |
| Commercial 2,4-D | Tomato Plants, Mustard, Rye | 62% | 80% | 100% | 100% |
| 2,4,5-T | Tomato Plants, Mustard, Rye | 51% | 76% | 100% | 100% |
| Dicamba | Tomato Plants, Mustard, Rye | 54% | 79% | 99% | 100% |
| Water-degradable compositions 2,4-D | Tomato Plants, Mustard, Rye | 0% | 0% | 0% | 0% |
| 2,4,5-T | Tomato Plants, Mustard, Rye | 0% | 0% | 0% | 0% |
| Dicamba | Tomato Plants, Mustard, Rye | 0% | 0% | 0% | 0% |

As can clearly be seen from examining the above data, the compositions herein exhibited undectable lateral mobility as evidenced by the fact that even after the 9th day there was no detectable kill rate on the plants. Thus it can be easily seen that herbicides, and the like can be applied in a given area without fear that even under relatively high rainfall rates they will migrate from the area of application. This of course greatly minimizes pollution of water sheds under heavy rainfall conditions when herbicides are applied to a given area and moreover prevents a given herbicide or the like applied in one area from migrating to another area where it is desired that no herbicide or the like be present.

EXAMPLE 4

To demonstrate the non-leeching characteristic of the compounds produced herein, materials containing water degradable compositions of urea, cinnamic aldehyde, 2,4D, 2,4,5-T and dicamba were prepared in accordance with methods set out above. Soil columns 6 inches in length were set up and commercially available herbicides corresponding to the three above mentioned were placed on top of the soil columns. This was also done with the corresponding prepared preparations. In all cases, the amounts of the active ingredient were equal. Water equivalent to 3 inches of rain per day was added. After the first simulated rain, the commercial preparations of the 2,4-D, 2,4,5-T and dicamba all leeched through the columns. In the cases of the formulations prepared as per the present invention however, all the material was found to be within the top 1 inch of the soil column. The experiment was continued through what amounted to 30 inches of equivalent rain at which time it was still noted that the majority of the formulations were in the upper part of the soil column. As this example clearly indicates, the water degradable compounds of the present invention are quite effective in reducing pollution of underground water sources. Moreover, by remaining in the upper portion of the soil it will be recognized that maximum use of the herbicide, etc. will be achieved since the active ingredient will not be leeched through the soil.

EXAMPLE 5

A composition was prepared from urea, cinnamic aldehyde and a commercially available material known as Pramitol D.P. No. 1 (Pramitol) Concentrate sold by Chapman Chemical Co. Pramitol D.P. No. 1 Concentrate contains 1.79 lbs of 2,methoxy-4,6-bis (isopropylamino)-s-triazine, 0.66 lbs of pentachlorophenol and 0.96 lbs of 2,4-D dissolved in a petroleum oil. To one gallon of this Pramitol concentrate was added 21.3 gm of urea which was thoroughly dissolved. There was then added 2.1 gms of cinnamic aldehyde. The reaction was carried out at room temperature. To test the formulation thus formed from the Pramitol concentrate for its "anti-drift" characteristic, the following test was conducted: A vertical column was arranged in which a liquid or emulsion could be suspended. The column was equipped with a nozzle on the lowermost end and was pressurized with air such that the material contained in the column would be forced through the nozzle and be dispersed in the air in much the same manner that a liquid chemical being dropped from aircraft would be dispersed. Disposed perpendicularly to the column and beneath the nozzle was a constant velocity air source. Accordingly, when the material was ejected from the nozzle, the air from the constant velocity air source would cause it to drift in a direction away from the air source. This is a simulation of conditions which might be encountered when aircraft were dropping chemicals. The results of these drift experiments are shown in the tables below. In the first table the Pramitol concentrate was used as a standard and was compared with the concentrates having various additives commonly used to cut down the amount of drift and the composition formed from the Pramitol concentrate, urea and cinnamic aldehyde.

| Substance | Additive | Amount of Drift |
|---|---|---|
| Pramitol D.P.#1 Concentrate | None | 9 in. |
| Pramitol D.P.#1 Concentrate | ¾ g/gal soloid | 6 in. |
| Pramitol D.P.#1 Concentrate | 3 g/gal aluminum stearate | 6½ in. |
| Pramitol D.P.#1 Concentrate | 2.13 g/urea<br>0.23 g/cinnamic aldehyde | 4½ in. |

As can clearly be seen, the composition herein shows considerably less drift than the concentrate itself or the concentrate in combination with commonly used anti-drift agents.

In a like manner, the concentrate was diluted so as to form a spray which was compared in a similar fashion. The results are shown below.

Dilution of the Concentrate: one part concentrate to ten parts provalent 4A

| Substance | Additive | Amount of Drift |
|---|---|---|
| Pramitol Spray | None | 9 in. |
| Pramitol Spray | ¾ g/gal soloid | 6½–7 in. |
| Pramitol Spray | 3 g/gal aluminum stearate | 6½–7 in. |
| Pramitol Spray | 2.13 g/gal urea<br>0.23 g/cinnamic aldehyde | 4½–5 in. |

In addition, various concentrations of materials were studied. These results are shown below wherein all of the concentrates were diluted one part of concentrate to two parts of Provalent 4A. Provalent 4A (Mobil Co.) is a petroleum fraction comprised of 45% aliphatic material and 55% aromatic materials. In all cases shown below, the compositions were prepared as discussed above for the Pramitol concentrate.

| Substance | Additive | Amount of Drift |
|---|---|---|
| Pramitol D.P.#1 Spray | None | 9 in. |
| Pramitol D.P.#1 Spray | 2.13 g/urea<br>0.23 g/cinnamic aldehyde | 4½–5 in. |
| Pramitol D.P.#1 Spray | 1.5 g/urea<br>1.16 g/cinnamic aldehyde | 5½ in. |
| Pramitol D.P.#1 Spray | 1.0 g/urea<br>0.1 g/cinnamic aldehyde | 6–7 in. |
| Pramitol D.P.#1 Spray | 0.5 g/urea<br>.05 g/cinnamic aldehyde | 8–9 in. |

As the tables clearly show, the presence of the water degradable compositions in the Pramitol compositions whether as concentrates or sprays greatly reduces the amount of drift. The advantages of this are obvious when it is considered that in many cases, when aircraft are spraying given areas, high winds will cause the active ingredient to be carried to locals where it may cause detriment to both plant and wild life.

EXAMPLE 6

A material containing a water degradable composition comprising 2,4-D, bromacil, cinnamic aldehyde and urea was prepared in a concentrate form as follows: Urea (0.02 lbs) was dissolved in a minimum amount of methanol. To the urea solution was added 0.02 lbs of cinnamic aldehyde. Enough bromacil was then added to the solution to ensure that the final concentration of bromacil in the concentrate was 1 lb/gallon. Following the addition of the bromacil, 1 lb of the amine salt of 2,4-D was added. Pentachlorophenol (0.75 lbs) was added to the solution which was thoroughly mixed and enough methanol added to bring the final volume to 1 gallon. The solution was stirred until all material had completely dissolved. The preparation was carried out at room temperature and required approximately 30 minutes to ensure complete solution. The final composition produced contained chemically combined 2,4-D and encapsulated bromacil with an approximate release rate of 6 months. By warming the concentrate to 80° C. for 5 minutes, the molecular weight of the material could be increased giving a more viscous, sticky material requiring between 9 months and a year for degradation to occur. The concentrate thus prepared could be diluted 1:10 with Provalent 4A of diesel without the material precipitating out of solution. Using a proper surfactant, the concentrate could be formulated into an aqueous medium for spraying. As can be seen, this method allows the production of a herbicide containing two active ingredients.

EXAMPLE 7

A concentrate containing a water degradable composition containing 2,4-D, urea, cinnamic aldehyde and bromacil was prepared as follows: Urea (0.30 lbs) was dissolved in a minimum amount of methyl alcohol. To this was added 0.03 lbs of cinnamic aldehyde. 1.50 lbs of 2,4-D (amine salt) was then added followed by sufficient bromacil to make a 1.50 lb/gallon concentration of bromacil in the final concentrate. Pentachlorophenol (0.75 lbs) was then added and the mixture was brought to a volume of 1 gallon with a solvent comprised of 90% Provalent 4A and 10% butyl alcohol. The reaction was carried out at room temperature and required about 30 minutes of agitation to ensure complete solution of the active ingredients. The concentrate contained chamically bound 2,4-D and encapsulated bromacil with an approximate release rate of 6 months. By heating the concentrate to 80° C. for a period of 5 minutes a material is obtained which will require between 9 months and a year for complete degradation to occur. It was found that this material could be changed, by heating, from a viscous liquid to a super cooled liquid similar to window glass. The concentrate thus prepared may be diluted 1:10 with Provalent 4A, diesel oil or other such solvents without the active ingredients precipitating out of solution. By adding the proper surfactant and the required amount of concentrate to water, an aqueous spray can be produced which has a reasonable amount of stability in terms of non-degradability.

EXAMPLE 8

To demonstrate the effectiveness of the water degradable compositions of the present invention wherein a herbicidally active compound forms part of the compound, various herbicides were reacted with urea and cinnamaldehyde in accordance with the above examples. The compositions were made into aqueous solutions suitable for spraying. The aqueous sprayable compositions were formulated such that they were applied at a rate of 20 gallons per acre. The succeeding examples show the kill rates on various forms of weeds using various herbicides at various levels of the active ingredient per acre. In all cases, the rate refers to the amount of the active ingredient, i.e. the herbicides, per acre. In all cases, comparison was made between a commercial sprayable composition applied in the same fashion and in amount so as to give the same amount of active ingredient per acre. The designations Co and Po refer to the commercial and the prepared compositions, respectively.

| | Kill Rate After 16 Days Rate - ¼ lb/acre | | | | | | | | | | | |
|---|---|---|---|---|---|---|---|---|---|---|---|---|
| | Co | Po | Co | Po | Co | Po | Co | Po | Co | Po | Co | Po |
| WEEDS | Dicamba | | 2,3,6 TBA | | T.C.A. | | Dalapon Na salt | | 2,4-D | | 2,4,5-T | |
| Ragweed | 81 | 100 | 63 | 89 | 19 | 73 | 28 | 100 | 27 | 100 | 29 | 100 |
| Iron Weed | 42 | 90 | 12 | 76 | 18 | 68 | 17 | 73 | 32 | 73 | 31 | 100 |
| Stinkweed | 30 | 80 | 33 | 83 | 11 | 61 | 11 | 80 | 11 | 100 | 12 | 100 |
| Silva Ragweed | 63 | 100 | 58 | 92 | 16 | 72 | 32 | 100 | 24 | 100 | 26 | 100 |
| Bindweed | 0 | 80 | 49 | 100 | 0 | 19 | 4 | 44 | 16 | 100 | 14 | 100 |
| Milkweed | 67 | 83 | 66 | 100 | 6 | 39 | 11 | 26 | 22 | 100 | 24 | 100 |
| Dandelion | 42 | 100 | 46 | 100 | 2 | 33 | 29 | 79 | 33 | 100 | 42 | 100 |
| Musk Thistle | 10 | 90 | 17 | 97 | 0 | 29 | 14 | 63 | 4 | 100 | 12 | 100 |
| Marijuana | 10 | 82 | 18 | 73 | 0 | 3 | 7 | 17 | 8 | 100 | 16 | 100 |

TABLE II

| | | 2,3,6-TBA | | | | | | | | | | | | | | |
|---|---|---|---|---|---|---|---|---|---|---|---|---|---|---|---|---|
| | | Rate - lb/acre % Kill - 5 days | | | | | | | | Rate - lb/acre % Kill - 30 days | | | | | | |
| WEEDS | Material | 1/32 | 1/16 | ⅛ | ¼ | ⅜ | ½ | 1 | 1¼ | 1/32 | 1/16 | ⅛ | ¼ | ⅜ | ½ | 1 | 1¼ |
| Ragweed | Po | 78 | 85 | 92 | 100 | 100 | 100 | 100 | 100 | 88 | 97 | 100 | 100 | 100 | 100 | 100 | 100 |
| | Co | 11 | 17 | 25 | 29 | 39 | 51 | 63 | 72 | 9 | 14 | 21 | 29 | 38 | 47 | 56 | 69 |
| Iron Weed | Po | 70 | 81 | 89 | 92 | 96 | 100 | 100 | 100 | 72 | 84 | 96 | 100 | 100 | 100 | 100 | 100 |
| | Co | 0 | 6 | 12 | 26 | 39 | 47 | 56 | 61 | 0 | 4 | 11 | 26 | 37 | 49 | 58 | 64 |
| Stinkweed | Po | 44 | 55 | 59 | 60 | 68 | 75 | 83 | 100 | 76 | 89 | 92 | 100 | 100 | 100 | 100 | 100 |
| | Co | 0 | 4 | 8 | 17 | 23 | 30 | 37 | 42 | 0 | 5 | 11 | 20 | 29 | 36 | 47 | 58 |
| Silver Ragweed | Po | 76 | 83 | 94 | 100 | 100 | 100 | 100 | 100 | 89 | 99 | 100 | 100 | 100 | 100 | 100 | 100 |
| | Co | 9 | 14 | 23 | 27 | 34 | 42 | 51 | 59 | 11 | 17 | 28 | 38 | 49 | 54 | 66 | 76 |
| Bindweed | Po | 59 | 64 | 76 | 87 | 91 | 97 | 100 | 100 | 69 | 84 | 99 | 100 | 100 | 100 | 100 | 100 |
| | Co | 0 | 3 | 7 | 17 | 21 | 26 | 33 | 39 | 0 | 2 | 9 | 19 | 26 | 31 | 42 | 47 |
| Dandelion | Po | 72 | 87 | 91 | 100 | 100 | 100 | 100 | 100 | 88 | 100 | 100 | 100 | 100 | 100 | 100 | 100 |
| | Co | 11 | 15 | 23 | 36 | 49 | 69 | 82 | 100 | 15 | 27 | 39 | 51 | 68 | 79 | 94 | 100 |
| Milk Weed | Po | 86 | 91 | 97 | 100 | 100 | 100 | 100 | 100 | 92 | 100 | 100 | 100 | 100 | 100 | 100 | 100 |
| | Co | 13 | 17 | 26 | 39 | 51 | 70 | 88 | 100 | 15 | 23 | 29 | 42 | 56 | 72 | 91 | 100 |

TABLE III

| | | 2,4,5-T | | | | | | | | | | | | | | |
|---|---|---|---|---|---|---|---|---|---|---|---|---|---|---|---|---|
| | | Rate - lb/acre % Kill - 5 days | | | | | | | | Rate - lb/acre % Kill - 30 days | | | | | | |
| WEEDS | Material | 1/32 | 1/16 | ⅛ | ¼ | ⅜ | ½ | 1 | 1¼ | 1/32 | 1/16 | ⅛ | ¼ | ⅜ | ½ | 1 | 1¼ |
| Ragweed | Po | 78 | 89 | 96 | 100 | 100 | 100 | 100 | 100 | 88 | 96 | 100 | 100 | 100 | 100 | 100 | 100 |
| | Co | 2 | 11 | 26 | 39 | 58 | 66 | 70 | 72 | 3 | 12 | 30 | 48 | 61 | 69 | 71 | 79 |
| Iron Weed | Po | 61 | 69 | 76 | 83 | 89 | 94 | 98 | 100 | 69 | 77 | 94 | 100 | 100 | 100 | 100 | 100 |
| | Co | 4 | 8 | 17 | 22 | 27 | 33 | 39 | 46 | 0 | 4 | 8 | 23 | 39 | 48 | 57 | 63 |
| Stinkweed | Po | 66 | 81 | 94 | 100 | 100 | 100 | 100 | 100 | 79 | 88 | 97 | 100 | 100 | 100 | 100 | 100 |
| | Co | 7 | 11 | 18 | 23 | 26 | 29 | 31 | 34 | 0 | 3 | 9 | 17 | 26 | 37 | 44 | 49 |
| Silver Ragweed | Po | 76 | 88 | 94 | 100 | 100 | 100 | 100 | 100 | 86 | 95 | 99 | 100 | 100 | 100 | 100 | 100 |
| | Co | 10 | 17 | 24 | 31 | 36 | 41 | 45 | 47 | 2 | 13 | 19 | 27 | 35 | 44 | 49 | 56 |
| Bindweed | Po | 51 | 55 | 61 | 68 | 73 | 88 | 99 | 100 | 82 | 91 | 99 | 100 | 100 | 100 | 100 | 100 |
| | Co | 0 | 0 | 3 | 7 | 14 | 21 | 27 | 33 | 0 | 0 | 0 | 4 | 18 | 29 | 34 | 42 |
| Dandelion | Po | 89 | 98 | 100 | 100 | 100 | 100 | 100 | 100 | 93 | 100 | 100 | 100 | 100 | 100 | 100 | 100 |
| | Co | 11 | 13 | 22 | 28 | 33 | 39 | 42 | 47 | 9 | 15 | 23 | 29 | 34 | 41 | 43 | 49 |
| Milk Weed | Po | 92 | 97 | 100 | 100 | 100 | 100 | 100 | 100 | 86 | 94 | 100 | 100 | 100 | 100 | 100 | 100 |
| | Co | 9 | 18 | 26 | 32 | 39 | 41 | 45 | 58 | 11 | 19 | 27 | 35 | 42 | 49 | 56 | 67 |

TABLE IV

| | | 2,4-D | | | | | | | | | | | | | | |
|---|---|---|---|---|---|---|---|---|---|---|---|---|---|---|---|---|
| | | Rate - lb/acre % Kill - 5 Days | | | | | | | | Rate - lb/acre % Kill - 30 Days | | | | | | |
| WEEDS | Material | 1/32 | 1/16 | ⅛ | ¼ | ⅜ | ½ | 1 | 1¼ | 1/32 | 1/16 | ⅛ | ¼ | ⅜ | ½ | 1 | 1¼ |
| Ragweed | Po | 63 | 74 | 82 | 97 | 99 | 100 | 100 | 100 | 88 | 96 | 100 | 100 | 100 | 100 | 100 | 100 |

TABLE IV-continued

| | | 2,4-D | | | | | | | | | | | | | | |
|---|---|---|---|---|---|---|---|---|---|---|---|---|---|---|---|---|
| | | Rate - lb/acre % Kill - 5 Days | | | | | | | | Rate - lb/acre % Kill - 30 Days | | | | | | |
| WEEDS | Material | 1/32 | 1/16 | 1/8 | 1/4 | 1/2 | 3/4 | 1 | 1¼ | 1/32 | 1/16 | 1/8 | 1/4 | 1/2 | 3/4 | 1 | 1¼ |
| | Co | 3 | 12 | 20 | 32 | 42 | 53 | 61 | 70 | 2 | 18 | 23 | 35 | 45 | 57 | 66 | 76 |
| Iron Weed | Po | 41 | 56 | 65 | 76 | 82 | 99 | 100 | 100 | 71 | 83 | 94 | 100 | 100 | 100 | 100 | 100 |
| | Co | 5 | 9 | 23 | 27 | 31 | 39 | 42 | 45 | 1 | 9 | 19 | 26 | 38 | 46 | 52 | 58 |
| Stinkweed | Po | 39 | 53 | 61 | 76 | 88 | 99 | 100 | 100 | 57 | 69 | 82 | 100 | 100 | 100 | 100 | 100 |
| | Co | 7 | 9 | 14 | 17 | 21 | 23 | 26 | 30 | 0 | 5 | 9 | 13 | 19 | 26 | 39 | 43 |
| Silver Ragweed | Po | 65 | 76 | 80 | 83 | 96 | 100 | 100 | 100 | 70 | 82 | 97 | 100 | 100 | 100 | 100 | 100 |
| Bindweed | Co | 9 | 17 | 23 | 31 | 37 | 39 | 44 | 45 | 0 | 12 | 19 | 25 | 29 | 36 | 41 | 49 |
| | Po | 51 | 61 | 68 | 72 | 86 | 92 | 100 | 100 | 59 | 72 | 89 | 100 | 100 | 100 | 100 | 100 |
| | Co | 0 | 1 | 9 | 11 | 17 | 23 | 27 | 31 | 0 | 0 | 5 | 19 | 26 | 31 | 38 | 39 |
| Dandelion | Po | 59 | 69 | 80 | 91 | 96 | 100 | 100 | 100 | 63 | 71 | 89 | 100 | 100 | 100 | 100 | 100 |
| | Co | 9 | 12 | 17 | 23 | 27 | 31 | 37 | 44 | 3 | 6 | 11 | 19 | 26 | 33 | 40 | 45 |
| Milk Weed | Po | 66 | 72 | 81 | 88 | 92 | 100 | 100 | 100 | 84 | 91 | 99 | 100 | 100 | 100 | 100 | 100 |
| | Co | 11 | 14 | 19 | 22 | 26 | 33 | 37 | 41 | 9 | 11 | 17 | 23 | 30 | 42 | 51 | 64 |

EXAMPLE 9

A formulation containing a water-degradable compound comprising 2,4-D, urea and crotonaldehyde was prepared as per the procedure of Example 1. The ingredients were present in amounts so as to give a molar ratio of 2,4-D to urea to crotonaldehyde of 2:1:2, respectively. The solution was heated to 175° C. The material which was obtained, after evaporation of the solvent, was a reddish-brown, tacky material which contained, according to a UV spectrophotometric method, approximately 68% of 2,4-D. An amount of 0.28976 gm of the material was deposited in a thin film on a 5 cm filter paper which was then suspended in 50 ml of tap water. Each day, the filter paper containing the material was transferred to a fresh 50 ml of water and the previous 50 ml of water analyzed, by the UV spectrophotometric method, to determine the amount of aldehyde and/or 2,4-D which had been released. The results are shown in Table V.

TABLE V

| Days | Wt. 2,4-D/day gms. | Total Wt. 2,4-D gms. | Total % 2,4-D Released |
|---|---|---|---|
| 1 | | 0.04859 | 18.1 |
| 2 | 0.04069 | 0.08928 | 33.3 |
| 3 | 0.03791 | 0.12719 | 47.4 |
| 4 | 0.03733 | 0.16452 | 61.3 |
| 5 | 0.03850 | 0.20302 | 75.7 |
| 6 | 0.02841 | 0.23143 | 86.2 |
| 7 | 0.01455 | 0.24598 | 91.7 |
| 8 | 0.01036 | 0.25634 | 95.5 |
| 9 | 0.00678 | 0.26312 | 98.1 |
| 10 | 0.00410 | 0.26722 | 99.6 |
| 11 | 0.00350 | 0.27072 | 100.9[1] |
| 12 | 0.00316 | 0.27388 | 102.1[1] |
| 13 | 0.00259 | 0.27647 | 103.0[1] |
| 14 | 0.00207 | 0.27854 | 103.8[1] |
| 15 | 0.00227 | 0.28081 | 104.6[1] |
| 16 | 0.00231 | 0.28312 | 105.5[1] |
| 17 | 0.00213 | 0.28525 | 106.3[1] |

[1]Values greater than 100% due to experimental error in analytical technique.

EXAMPLE 10

The procedure of Example 1 was followed except the material was prepared from the 2,4-D amine salt and cinnamic aldehyde in a 1:1 molar ratio at a temperature of 125° C. The resulting solvent free material contained approximately 56% 2,4-D. The release rate results are shown in Table VI.

As the results of Examples 13–15 and Tables V and VI show, the water degradable materials prepared as per the present invention exhibit immediate release of the biologically active material, i.e. the 2,4-D along with sustained release of same.

TABLE VI

| Days | Wt. 2,4-D/day gms. | Total Wt. 2,4-D gms. | Total % 2,4-D Released |
|---|---|---|---|
| 1 | 0.32979 | 0.32979 | 80.4 |
| 2 | 0.01044 | 0.34023 | 83.0 |
| 3 | 0.00528 | 0.34551 | 84.3 |
| 4 | 0.00324 | 0.34875 | 85.1 |
| 5 | 0.00218 | 0.35093 | 85.6 |
| 6 | 0.00238 | 0.35331 | 86.2 |
| 7 | 0.00264 | 0.35595 | 86.8 |
| 8 | 0.00175 | 0.35770 | 87.2 |
| 9 | 0.00167 | 0.35937 | 87.7 |
| 10 | 0.00139 | 0.36076 | 88.0 |
| 11 | 0.00129 | 0.36205 | 88.3 |
| 12 | 0.00132 | 0.36337 | 88.6 |
| 13 | 0.00139 | 0.36476 | 89.0 |
| 14 | 0.00142 | 0.36618 | 89.3 |
| 15 | 0.00128 | 0.36746 | 89.6 |
| 16 | 0.00105 | 0.36851 | 89.9 |
| 17 | 0.00051 | 0.36902 | 90.0 |
| 18 | 0.00050 | 0.36952 | 90.1 |
| 19 | 0.00048 | 0.37000 | 90.2 |
| 20 | 0.00038 | 0.37038 | 90.3 |
| 21 | 0.00092 | 0.37130 | 90.6 |

EXAMPLE 11

Using the general procedure of Example 1 a water-degradable composition was prepared from 2,4-D, urea and cinnamaldehyde employing molar ratios of 2,4-D to urea to cinnamaldehyde of 2:1:2, respectively. To ensure completeness of reaction, i.e. ester formation, the reaction mixture was refluxed at 180° C. for eight days. Subsequent infrared analysis revealed that virtual completion of the reaction had occurred, i.e. the 2,4-D, urea and cinnamaldehyde were chemically bound in the ester structure described above. The material contained approximately 57% of 2,4-D. The release rate data of the 2,4-D and the aldehyde from the water degradable composition are shown in Table VII.

TABLE VII

| Days | Wt. 2,4-D/day gms. | Total Wt. 2,4-D gms. | Wt. Aldehyde/day gms. | Total Wt. Adlehyde gms. | Total % 2,4-D Released |
| --- | --- | --- | --- | --- | --- |
| 1 | 0.00026 | 0.00026 | 0.00003 | 0.00003 | 0.05 |
| 2 | 0.00053 | 0.00079 | 0.00006 | 0.00009 | 0.15 |
| 3 | 0.00055 | 0.00134 | 0.00006 | 0.00015 | 0.26 |
| 4 | 0.00059 | 0.00193 | 0.00005 | 0.00020 | 0.37 |
| 5 | 0.00081 | 0.00274 | 0.00008 | 0.00028 | 0.52 |
| 6 | 0.00060 | 0.00334 | 0.00006 | 0.00034 | 0.64 |
| 7 | 0.00053 | 0.00387 | 0.00005 | 0.00039 | 0.74 |
| 8 | 0.00044 | 0.00431 | 0.00005 | 0.00044 | 0.82 |
| 9 | 0.00062 | 0.00493 | 0.00006 | 0.00050 | 0.94 |
| 10 | 0.00068 | 0.00561 | 0.00006 | 0.00056 | 1.07 |
| 11 | 0.00065 | 0.00626 | 0.00006 | 0.00062 | 1.20 |

EXAMPLE 12

The procedure of Example 11 was followed, the same ratios of components and the same temperatures being employed in the reaction. The resulting material was found to contain approximately 57% 2,4-D. The release rate data of the 2,4-D and the aldehyde from the composition are shown in Table VIII. As can be seen from reviewing the results of Examples 11 and 12 and Tables VII and VIII, the water-degradable composition, i.e. the complex esters described above, releases the active ingredient very slowly. It can thus be seen, and as demonstrated by the other examples, that the mixture of unreacted biologically active agent and chemically combined active agent results in a formulation which upon application provides immediate action of the free biologically active agent and sustained long lasting effect due to slow degradation or hydrolysis of the water-degradable compound. It can thus be seen that the compositions and formulations of the present invention are ideally suited for the uses set out above.

TABLE VIII

| Days | Wt. 2,4-D/day gms. | Total Wt. 2,4-D gms. | Wt. Aldehyde/day gms. | Total Wt. Aldehyde gms. | Total % 2,4-D Released |
| --- | --- | --- | --- | --- | --- |
| 1 | 0.00024 | 0.00004 | 0.00003 | 0.00003 | 0.048 |
| 2 | 0.00052 | 0.00076 | 0.00006 | 0.00009 | 0.15 |
| 3 | 0.00070 | 0.00146 | 0.00006 | 0.00015 | 0.29 |
| 4 | 0.00056 | 0.00202 | 0.00005 | 0.00020 | 0.40 |
| 5 | 0.00063 | 0.00265 | 0.00006 | 0.00026 | 0.53 |
| 6 | 0.00069 | 0.00334 | 0.00007 | 0.00033 | 0.67 |
| 7 | 0.00060 | 0.00394 | 0.00006 | 0.00039 | 0.79 |
| 8 | 0.00052 | 0.00446 | 0.00005 | 0.00044 | 0.89 |
| 9 | 0.00068 | 0.00514 | 0.00007 | 0.00051 | 1.02 |
| 10 | 0.00072 | 0.00586 | 0.00006 | 0.00057 | 1.17 |
| 11 | 0.00061 | 0.00647 | 0.00006 | 0.00063 | 1.29 |

A series of water-degradable compounds according to the present invention was prepared using various combinations of hydrazine or urea; cinnamic aldehyde or crotonaldehyde; and various aromatic carboxylic acids. The general method of preparation was as follows: 0.2 mole of the aldehyde, 0.2 mole of the carboxylic cid and 0.1 mole of the hydrazine or urea were mixed together in an acetone solution. The solution was heated to between 65° and 120° C. until the characteristics reddish brown color was obtained. The reaction product was then recovered by vacuum removal of the acetone. Molecular weight determinations using freezing point depression and infrared spectra were obtained on the compounds prepared. In determining release rates of the carboxylic acids from the water degradable compounds, the following procedure was employed: the water degradable compounds were dissolved in acetone. A small portion of the acetone solution was then deposited on filter paper and the acetone removed leaving a residue of the water-degradable compound on the filter paper. The amount of the water-degradable compound deposited was determined by weighment before and after addition of the acetone solution to the filter paper. The coated filter paper was then suspended in 100 ml of distilled water. At suitable intervals the distilled water was replaced and analyzed by a UV spectrophotometric method to determine the amount of the carboxylic acid (herbicide) released from the water-degradable compound.

EXAMPLE 13

A water degradable compound was prepared from 2,4-D, hydrazine and cinnamic aldehyde. Molecular weight determinations and IR spectra establish that the compound prepared had the following structure:

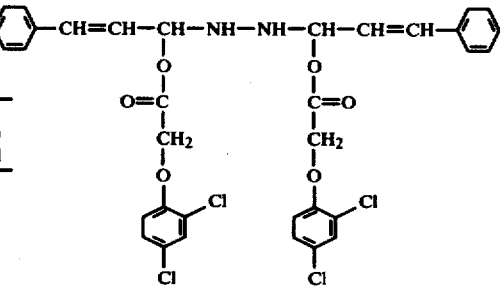

The release data is shown below:

| Time | Wt. deposited: 0.5691g Wt. acid: 0.3583g | | |
|---|---|---|---|
| | PPH 2,4-D | % 2,4-D Released | Total % 2,4-D Released |
| 24 Hr. | 330 | 5.80 | 5.80 |
| 54 Hr. | 14.5 | 0.40 | 6.20 |
| 126 Hr. | 62.1 | 1.73 | 7.93 |
| 2 Months | 591 | 16.5 | 24.4 |

EXAMPLE 14

A water-degradable compound was prepared from 2,4-D, hydrazine and crotonaldehyde. Molecular weight determinations and IR spectra establish that the compound had the following structure:

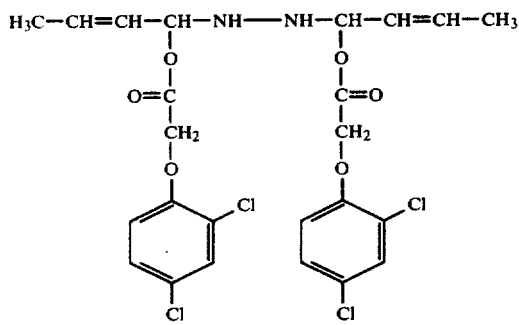

The release data is shown below:

| Time | Wt. deposited: 0.7057g Wt. acid: 0.5397g | | |
|---|---|---|---|
| | PPH 2,4-D | % 2,4-D Released | Total % 2,4-D Released |
| 24 Hr | 382 | 7.08 | 7.08 |
| 54 Hr | 101 | 1.87 | 8.95 |
| 126 Hr | 125 | 2.32 | 11.27 |
| 2 Months | 125 | 2.32 | 13.59 |

EXAMPLE 15

Urea, cinnamic aldehyde and 2,4-D were used to prepared a water-degradable compound of the following formula:

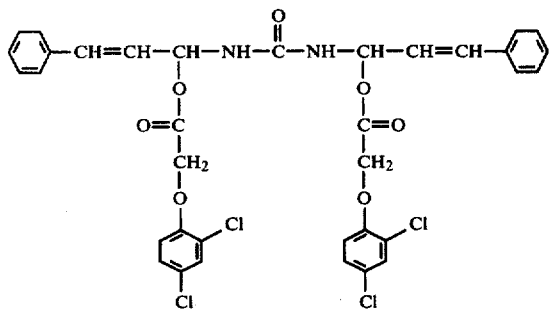

That the structure is, as shown above, is substantiated by molecular weight determinations and IR spectra.

EXAMPLE 16

A herbicidally active, water-degradable compound was prepared from 2,4-D, urea and crotonaldehyde and was shown by molecular weight determination and IR spectra to have the following structure:

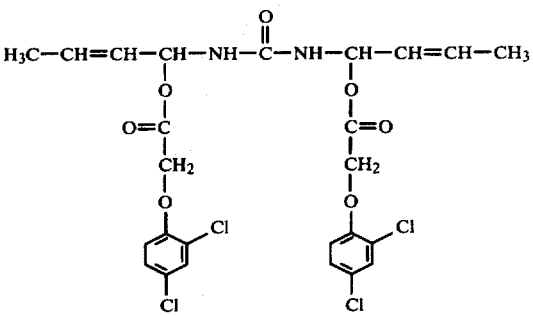

EXAMPLE 17

A water-degradable compound was prepared from 2-methoxy-3,6-dichlorobenzoic acid (Dicamba), hydrazine and cinnamic aldehyde. Using molecular weight determinations and IR spectra, the structure of the compound was found to be as follows:

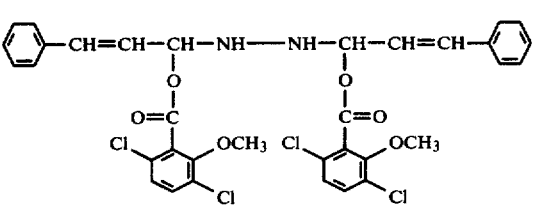

EXAMPLE 18

A water-degradable compound was prepared from Dicamba, hydrazine and crotonaldehyde. The structure of the compound, as determined from molecular weight and IR spectra, was as follows:

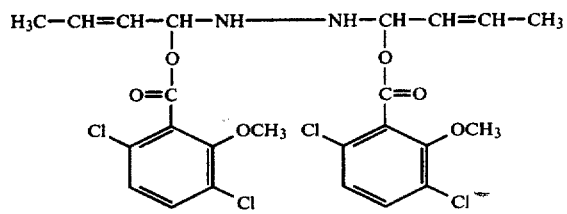

Release data are shown below:

| Time | Wt. Deposited: 0.4794g Wt. Acid: 0.3018g | | |
|---|---|---|---|
| | PPM Dicamba | % Dicamba Released | Total % Dicamba Released |
| 24 Hr | 273 | 9.05 | 9.05 |
| 54 Hr | 55.7 | 1.84 | 10.1 |
| 126 Hr | 19.1 | 0.63 | 10.7 |
| 2 Months | 457 | 15.14 | 25.8 |

EXAMPLE 19

A water-degradable compound prepared from Dicamba, urea and cinnamic aldehyde was prepared. Molecular weight determinations and IR spectra establish the structure of the compound as follows:

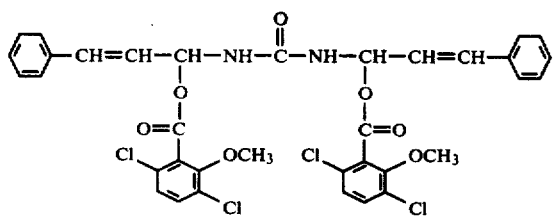

The release data is shown below:

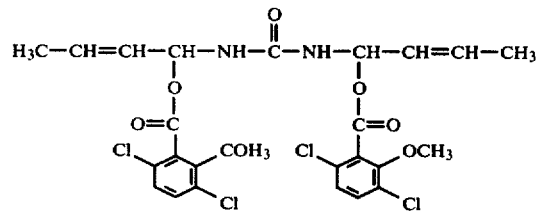

EXAMPLE 20

A water-degradable compound was prepared using Dicamba, urea and crotonaldehyde and was found, by molecular weight determinations and IR spectra, to have the following structure:

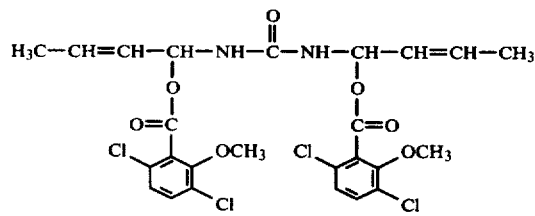

The release data are shown below:

| Time | Wt. deposited: 0.6192g Wt. acid: 0.4510g | | |
|---|---|---|---|
| | PPH Dicamba | % Dicamba Released | Total % Dicamba Released |
| 24 Hr. | 602 | 13.3 | 13.3 |
| 54 Hr. | 421 | 9.3 | 22.6 |
| 126 Hr. | 169 | 3.7 | 26.3 |
| 2 Months | 896 | 19.8 | 46.2 |

EXAMPLE 21

A water-degradable compound was prepared from 3-amino-2,5-dichlorobenzoic acid (Amiben), hydrazine and cinnamic aldehyde. IR spectra of the compound indicated that the formula was as follows:

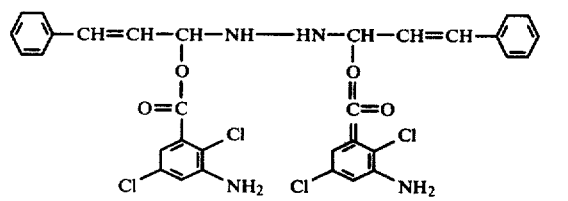

The release data is shown below:

| Time | Wt. deposited: 0.7138g Wt. acid: 0.4376g | | |
|---|---|---|---|
| | PPH Chloramben | % Chloramben Released | Total % Chloramben Released |
| 24 Hr. | 45.3 | 1.03 | 1.03 |
| 54 Hr. | 81.3 | 1.97 | 3.00 |
| 126 Hr. | 38.9 | 0.89 | 3.89 |
| 2 Months | 205 | 4.68 | 8.57 |

EXAMPLE 22

A water-degradable compound containing Amiben (Chloramben) hydrazine and crotonaldehyde was prepared. Molecular weight determinations and IR spectra indicated that the structure was as follows:

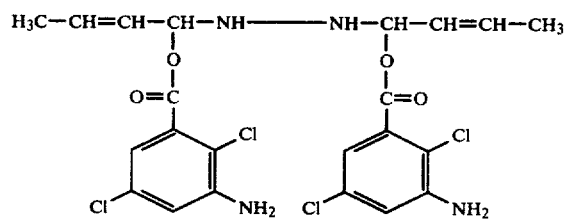

The release data is shown below:

| Time | Wt. deposited: 0.5872g Wt. acid: 0.4415g | | |
|---|---|---|---|
| | PPM Chloramben | % Chloramben Released | Total % Chloramben Released |
| 24 Hr. | 359 | 8.131 | 8.13 |
| 54 Hr. | 384 | 8.698 | 16.8 |
| 126 Hr. | 308 | 6.976 | 23.8 |
| 2 Months | 803 | 18.188 | 42.0 |

EXAMPLE 23

Amiben, urea and cinnamic aldehyde were used to prepare a water-degradable compound, which, according to infrared spectra, was determined to have the following structure:

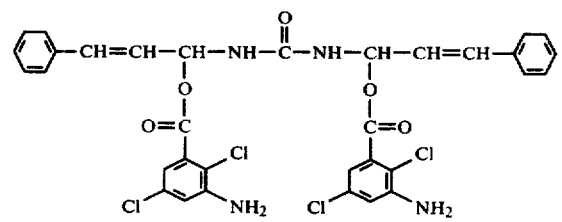

EXAMPLE 24

A water-degradable compound prepared from Amiben, urea and crotonaldehyde was prepared. Molecular weight determinations and IR spectra establish that the compound had the following structure:

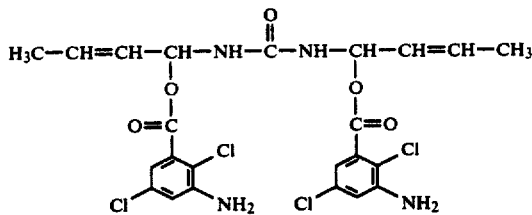

Using the same procedure as employed for Examples 13-24, water-degradable compounds are prepared from hydrazine or urea; crotonaldehyde or cinnamic aldehyde; and carboxylic acids such as benzoic acid, 4-amino-3,5,6-trichloropicolinic acid, 2-methoxy-3,5,6-trichlorobenzoic acid, 2-methyl-4-chlorophenoxyacetic acid, 2-(2-methyl-4-chlorophenoxy) propionic acid, phenoxyacetic acid, and 2-phenoxy propionic acid. In all cases, the water degradable compounds are found to have the structure depicted by the general Formula I above and as exemplified more specifically in the structures depicted in Examples 13-24.

We claim:

1. A water-degradeable compound having the formula

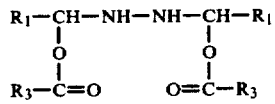

wherein $R_1$ is selected from the class consisting of

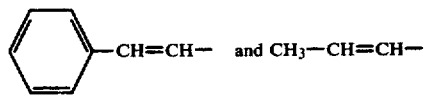

and $R_3$ is selected from the class consisting of

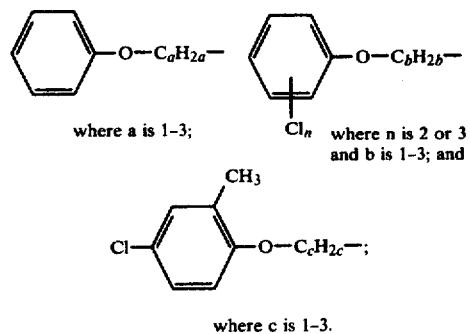

where c is 1-3.

2. The compound of claim 1 wherein $R_1$ is

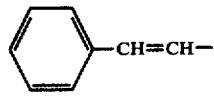

3. The compound of claim 1 wherein $R_1$ is $H_3C-CH=CH-$

4. The compound of claim 1 wherein $R_3$ has the structure

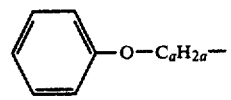

where a is 1-3.

5. The compound of claim 1 wherein $R_3$ has the structure

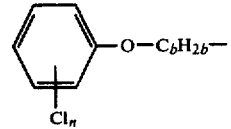

where b is 1-3 and n is 2 or 3.

6. The compound of claim 1 wherein $R_3$ is

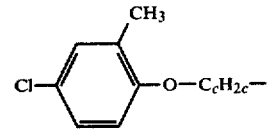

where c is 1-3.

7. A water-degradeable compound produced by the process comprising, contacting, in a solvent medium,
(a) hydrazine;
(b) an aldehyde selected from the class consisting of cinnamic aldehyde and crotonaldehyde; and
(c) a carboxylic acid compound selected from the class consisting of

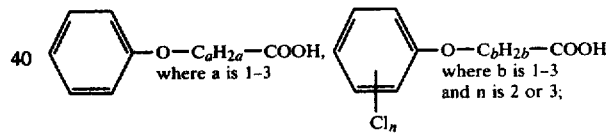

2-methyl-4-chlorophenoxyacetic acid; and 2-(2-methyl-4-chlorophenoxy) propionic acid.

8. The compound of claim 7 wherein said solvent in said process comprises an aqueous medium.

9. The compound of claim 7 wherein said solvent in said process comprises an organic medium.

10. The compound of claim 7 wherein said contacting in said process is carried out at a temperature of from about 30° to about 180° C.

11. The compound of claim 7 wherein said aldehyde in said process is cinnamic aldehyde.

12. The compound of claim 7 wherein said aldehyde in said process is crotonaldehyde.

13. The compound of claim 7 wherein said carboxylic acid in said process has the structure

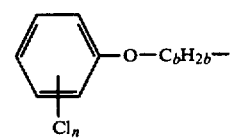

where b is 1-3 and n is 2 or 3.

* * * * *